United States Patent [19]

Staudenmaier et al.

[11] Patent Number: 5,739,017
[45] Date of Patent: Apr. 14, 1998

[54] PREPARATION OF 2-HYDROXYPHENYLACETIC ACID BY FERMENTATION

[75] Inventors: Horst Ralf Staudenmaier, Limburgerhof; Bernhard Hauer, Fussgoenheim; Wolfgang Ladner, Fussgoenheim; Ursula Mueller, Fussgoenheim; Uwe Pressler, Altrip; Joachim Meyer, Maxdorf, all of Germany

[73] Assignee: BASF Aktiengesellschaft, Ludwigshafen, Germany

[21] Appl. No.: 668,137

[22] Filed: Jun. 21, 1996

Related U.S. Application Data

[63] Continuation of Ser. No. 379,475, filed as PCT/EP93/02541, Sep. 20, 1993 published as WO94/08029 Apr. 14, 1994, abandoned.

[30] Foreign Application Priority Data

Sep. 29, 1992 [DE] Germany .......................... 42 32 522.6

[51] Int. Cl.$^6$ .................. C12P 7/42; C12N 1/14
[52] U.S. Cl. .............. 435/146; 435/254.1; 435/254.11; 435/911
[58] Field of Search .................... 435/254.11, 254.1, 435/146, 911

[56] References Cited

PUBLICATIONS

Phytochemistry 7, 1968, 1741–1742.

FEMS Microbiology Ltrs. 5, N4, 6, Jun. 1979.

*Primary Examiner*—Herbert J. Lilling
*Attorney, Agent, or Firm*—Keil & Weinkauf

[57] ABSTRACT

2-hydroxyphenylacetic acid is prepared from phenylacetic acid by fermentation with suitable microorganisms.

4 Claims, No Drawings

PREPARATION OF 2-HYDROXYPHENYLACETIC ACID BY FERMENTATION

This application is a continuation of application Ser. No. 08/379,475, filed as PCT/EP93/02541, Sep. 20, 1993 published as WO94/08029 Apr. 14, 1994, and now abandoned.

The present invention relates to a novel process for preparing 2-hydroxyphenylacetic acid from phenyl-acetic acid.

It is known that the breakdown of aromatic compounds by microorganisms frequently takes place via hydroxylated aromatic intermediates whose ring is subsequently cleaved with the introduction of further oxygen atoms.

One metabolic pathway for phenylacetic acid which is found in a number of fungi and bacteria gives 2-hydroxyphenylacetic acid as the first product. Then, in a second monohydroxylation, another OH group is introduced at position 5 or 6 of the aromatic ring. This reaction sequence has been found, for example, with *Aspergillus niger* and *Pseudomonas fluorescens* (Grazia Baggi et al., Styrene Catabolism by a Strain of *Pseudomonas fluorescens*, System. Appl. Microbiol. 4, 141–147, (1983); J. K. Faulkner and D. Woodcock, The Metabolism of Phenylacetic Acid by *Aspergillus niger*, Phytochemistry 7, 1741–1742, (1968); Fumiki Yoshizako et al., The Metabolism of Phenylacetic Acid by *Aspergillus fumigatus* ATCC 28282: Identification of 2,6-dihydroxyphenylacetic Acid, Can. J. Microbiol. 23, 1140–1142 (1977)).

These microorganisms are unsuitable for an economic process for preparing 2-hydroxyphenylacetic acid from phenylacetic acid because they produce small amounts of 2-hydroxyphenylacetic acid only as metabolic intermediate and immediately break it down further.

It is an object of the present invention to provide microorganisms which do not have the abovementioned disadvantages, and to make available a process for preparing 2-hydroxyphenylacetic acid from phenylacetic acid by fermentation using these microorganisms.

We have found that this object is achieved by microorganisms which, on the one hand, have the ability to hydroxylate phenylacetic acid in the ortho position but, on the other hand, do not transform the resultant 2-hydroxyphenylacetic acid further by, for example, using it as carbon source.

Microorganisms of this type are expediently obtained by mutation of wild-type strains which have the ability to break down phenylacetic acid via 2-hydroxyphenylacetic acid. Suitable wild-type strains are those of bacteria, actinomyces and fungi. Particularly suitable representatives are to be found, for example, in the following genera: Bacillus, Rhodococcus, Streptomyces, Absidia, Alternaria, Aspergillus, Beauveria, Botryodiplodia, Botrytis, Byssochlamys, Candida, Cephalosporium, Chaetomium, Cunninghamella, Curvularia, Dactylium, Drechslera, Epicoccum, Fusarium, Geotrichum, Gibberella, Gleophyllum, Gliocladium, Helminthosporium, Humicola, Hyphozyma, Metarrhizium, Microascus, Mucor, Neurospora, Paecilomyces, Penicillium, Phycomyces, Phyllosticta, Pythium, Rhizopus, Septoria, Sphaceloma, Trichoderma, Trichosporon, Trichurus, Verticillium.

Suitable microorganisms can easily be identified by the simple test described in Example 1.

It is expedient for mutants which are no longer able to break down 2-hydroxyphenylacetic acid to be generated or isolated from the suitable microorganisms.

Known microbiological techniques can be employed to generate such mutants. All conventional methods can be used to induce mutations, such as the use of mutagenic substances, eg. nitrosoguanidine, ethyl methanesulfonate, sodium nitrite, or the action of electromagnetic radiation such as UV, gamma or X-rays. It is additionally possible to use genetic elements which can undergo transpositioning for the mutagenesis. The property of the mutants of no longer growing on phenylacetic acid as sole C source can, for example, be utilized to isolate them.

We have found a novel fungus of the genus Humicola or Chaetomium which has been deposited under deposit number DSM 7047 at the Deutsche Sammlung von Mikroorganismen und Zellkulturen GmbH, Braunschweig, Federal Republic of Germany, on Nov. 8, 1991.

We have additionally found that the fungus DSM 7047 is particularly useful for the hydroxylation of aromatic compounds, especially of aromatic acids and acid derivatives. We have additionally found that cultivation of the fungus DSM 7047 in the presence of phenylacetic acid results in an advantageous process for preparing 2-hydroxyphenylacetic acid from phenylacetic acid.

The fungus DSM 7047 was identified by the CBS (Centraalbureau voor Schimmelcultures, Baarn, the Netherlands) as Humicola fuscoatra Traaen, while the DSM identified it as Chaetomium, presumably *Chaetomium seminudum*. Definitive assignment to the genus Humicola or Chaetomium is not possible at present. The strain DSM 7047 is distinguished in that it hydroxylates phenylacetic acid in the ortho position but does not metabolize the resulting 2-hydroxyphenylacetic acid.

To examine whether this is a general characteristic of the genera Humicola or Chaetomium, various strains of these genera were tested as described in Example 1:

| *Humicola brevispora* | ATCC 28403 |
| *" brunnea* | ATCC 22629 |
| *" fuscoatra* | ATCC 22723 |
| *" "* | ATCC 22721 |
| *" "* | Li 664 |
| *" grisea* | ATCC 22724 |
| *" "* | Li 193 |
| *" parvispora* | ATCC 22715 |
| *Chaetomium alba-avenulum* | Li 69 |
| *" globosum* | ATCC 6205 |
| *" "* | Li 70 |
| *" "* | Li 444 |

The strains identified by Li derive from the collection of strains at the agricultural trials station of BASF Aktiengesellschaft in Limburgerhof.

2-Hydroxyphenylacetic acid was detectable in small amounts with all these strains. However, it was always completely broken down again.

It was possible by mutagenesis with UV light to obtain from DSM 7047 in one step revertants which broke down phenylacetic acid in the same way as the Humicola and Chaetomium wild-type strains listed above. This showed that DSM 7047 is a mutant of an organism which breaks down phenylacetic acid.

The process according to the invention for preparing 2-hydroxyphenylacetic acid from phenylacetic acid comprises the cultivation of the suitable microorganisms in a conventional nutrient medium. Suitable nutrient media contain carbon sources, nitrogen sources, inorganic salts and, where appropriate, small amounts of trace elements and vitamins.

Nitrogen sources which can be used are inorganic or organic nitrogen compounds or materials which contain these compounds. Examples are ammonium salts, nitrates, corn steep liquor, brewers' yeast autolysate, soybean meal, wheat gluten, yeast extract, yeast, urea and potato protein.

Examples of carbon sources which can be used are sugars such as glucose, polyols such as glycerol or fats such as soybean oil. Examples of inorganic salts are the salts of calcium, magnesium, manganese, zinc, copper, iron and other metals. The phosphate ion should be particularly mentioned as anion of these salts. Where appropriate, growth factors such as biotin, riboflavin and other vitamins are added to the nutrient medium.

A particularly suitable nutrient medium is medium 2 described in Example 2.

Phenylacetic acid is added to the nutrient medium. Phenylacetic acid can be added in the form of the free acid or of a salt, preferably an alkali metal or ammonium salt, to the medium. Since the solubility of salts in aqueous nutrient media is generally greater than that of the free acid, the sodium or ammonium salt of phenylacetic acid is preferably used. The appropriate salt can expediently be prepared in situ by titrating the phenylacetic acid with a base.

The phenylacetic acid is usually added in amounts such that the concentration is adjusted to from 0.5 to 30 g, preferably from 1 to 20 g, per liter of nutrient medium.

The phenylacetic acid can be added to the nutrient medium at the start of the cultivation of the microorganism or during the cultivation in a plurality of portions or continuously.

It is additionally possible to retain the cultivated microorganism after the conversion is complete and to cultivate it further in fresh nutrient medium with phenylacetic acid.

This type of reuse of the biomass is a particularly advantageous embodiment of the process according to the invention because, for example, this saves the time for cultivating the biomass.

No other special conditions are needed for cultivating the microorganism. Thus, the cultivation can usually take place at from 20° to 40° C., preferably from 25° to 35° C.

The pH of the fermentation medium is kept at from 3 to 9 during the fermentation. A pH of from 4 to 7 is advantageous. Acidification of the medium during the fermentation can be compensated, for example, by adding a base such as ammonia.

The fermentation usually takes from 1 to 10 days in order to achieve maximum accumulation of the product in the fermentation medium.

The conversion can be easily established by taking a sample and analysing by, for example, gas chromatography. The isolation and purification of the 2-hydroxyphenylacetic acid from the nutrient medium can take place by conventional methods. It is expedient to separate the solid biomass from the nutrient medium, to extract the required substance with, for example, an organic solvent, where appropriate after previous acidification of the medium, and to isolate the required substance from the extracted phase.

The invention is illustrated further by the following examples.

EXAMPLE 1

Testing of microorganisms for ortho-hydroxylation of phenylacetic acid

Pure cultures of microorganisms from public collections of strains or from soil isolates (Drews: Mikrobiologisches Praktikum, 3rd edition, Springer Verlag 1976, pages 47–48) were tested to find whether they are able to hydroxylate phenylacetic acid specifically in the ortho position.

To do this, the strains were transferred from agar plates into liquid medium containing phenylacetic acid. The following medium was used (M1 medium):

| | |
|---|---|
| 10 g/l | glucose |
| 5 g/l | yeast extract (Difco) |
| 5 g/l | $(NH_4)_2SO_4$ |
| 0.5 g/l | $MgSO_4 \times 7H_2O$ |
| 0.05 g/l | $MnSO_4 \times 4H_2O$ |
| 2 ml/l | trace element solution |
| 1.5 g/l | $KH_2PO_4$ |
| 3.6 g/l | $K_2HPO_4$ |

Trace element solution:

| | |
|---|---|
| 200 mg/l | iron(II) sulfate 1-hydrate |
| 10 mg/l | zinc(II) sulfate 4-hydrate |
| 3 mg/l | manganese chloride 4-hydrate |
| 30 mg/l | boric acid |
| 20 mg/l | cobalt(II) chloride 6-hydrate |
| 1 mg/l | copper(II) chloride 2-hydrate |
| 2 mg/l | nickel(II) chloride 6-hydrate |
| 3 mg/l | sodium molybdate 2-hydrate |
| 500 mg/l | ethylenediaminetetraacetic acid (EDTA) |

The phenylacetic acid was made up into a 25% strength solution, titrated to pH 7 with NaOH, autoclaved and added to the medium which had been made up separately.

250 ml Erlenmeyer flasks were charged with 30 ml of M1 medium containing 1 g/l phenylacetic acid, inoculated in each case with one microorganism strain from agar plates, and incubated while shaking at 180 rpm and at 25° C. After 3, 7 and 10 days, 1 ml of the culture supernatant was removed, mixed with 100 µl of 5 N hydrochloric acid and 800 µl of ethyl acetate and vigorously mixed for 15 s. 700 µl of ethyl acetate phase were removed and evaporated under a gentle stream of nitrogen at 50° C. The residue was dissolved in 70 µl of ethyl acetate, and 50 µl of this was transferred into a sample tube for gas chromatography. 50 µl of N-methyl-N-tri-methylsilyltrifluoroacetamide (MSTFA) were added to and mixed with this. The samples were investigated by gas chromatography. An authentic sample of 2-hydroxyphenylacetic acid was used for comparison.

Production of 2-hydroxyphenylacetic acid was observed with strains from the following genera:

Fungi:

Absidia
Alternaria
Aspergillus
Beauveria
Botryodiplodia
Botrytis
Byssochlamys
Candida
Cephalosporium
Chaetomium
Cunninghamella
Curvularia
Dactylium
Drechslera
Epicoccum
Fusarium
Geotrichum
Gibberella
Gleophyllum
Gliocladium Helminthosporium
Humicola
Hyphozyma
Metarrhizium
Microascus
Mucor
Neurospora
Paecilomyces
Penicillium
Phycomyces
Phyllosticta
Pythium
Rhizopus
Septoria
Sphaceloma
Trichoderma
Trichosporon
Trichurus
Verticillium
Streptomyces:
  *Streptomyces aureofaciens*
  *Streptomyces hygroscopicus*
  *Streptomyces kasugaensis*
  *Streptomyces niveus*
  *Streptomyces roseochromogenus*
  *Streptomyces viridifaciens*
Bacteria:
  Bacillus
  Rhodococcus

EXAMPLE 2

Conversion of phenylacetic acid with DSM 7047
Medium 2:

| | |
|---|---|
| 50 g/l | glucose |
| 10 g/l | yeast extract (Difco) |
| 10 g/l | $(NH_4)_2SO_4$ |
| 0.5 g/l | $MgSO_4 \times 7H_2O$ |
| 3.6 g/l | $K_2HPO_4$ |
| 1.5 g/l | $KH_2PO_4$ |
| 10 ml/l | trace element solution |

Preculture: DSM 7047 was transferred from an agar plate into 150 ml of medium 2 containing 1 g/l phenylacetic acid and, in addition, 3 g/l Carbopol® 946 in a 1 l Erlenmeyer flask and shaken at 180 rpm and 30° C. for 3 days.

This preculture was used to inoculate a 1.5 l fermenter containing medium 2 and 5 g/l phenylacetic acid. In addition, 1 ml/l Pluriol P 2000 was added to prevent foaming.

The fermenter was maintained at 30° C., passing 1 l of air through per minute (=0.66 vvm) and stirring at 600 rpm.

After 5 days, the phenylacetic acid had been completely converted into 2-hydroxyphenylacetic acid.

The cells were removed by filtration through a cotton plug and were washed with 100 ml of water. The cell-free culture broth and the washings were combined and adjusted to pH 2 with HCl and were extracted twice with the same volume of tert-butyl methyl ether. Evaporation of the organic phase to dryness resulted in 8.2 g of residue which comprised 98% (determined by GC analysis) of 2-hydroxyphenylacetic acid. The structure of the product was confirmed by NMR.

EXAMPLE 3

Improved fermentation of DSM 7047

The preculture and inoculation of the fermenter were carried out as in Example 2; the pH of the fermentation medium fell from 6.8 to 5.6 during the fermentation. Further acidification was compensated by adding ammonia. As soon as the phenylacetic acid concentration had fallen to from 2.5 to 1 g/l, 1 g/l phenylacetic acid was metered in on four occasions. After 7 days the phenylacetic acid had been completely converted into 2-hydroxyphenylacetic acid.

We claim:

1. A process for preparing 2-hydroxyphenylacetic acid, which comprises cultivating a fungus on a solid growth medium, said fungus being able to hydroxylate phenylacetic acid in the ortho-position but being unable to metabolize 2-hydroxyphenylacetic acid , said fungus which is able to hydroxylate phenylacetic acid selected from the group consisting of the genera Absidia, Alternaria, Aspergillus, Beauveria, Botryodiplodia, Botrytis, Byssochlamys, Candida, Cephalosporium, Chaetomium, Cunninghamella, Curvularia, Dactylium, Drechslera, Epicoccum, Fusarium, Geotrichum, Gibberella, Gleophyllum, Gliocladium, Helminthosporium, Humicola, Hyphozyma, Metarrhizium, Micorascus, Mucor, Neurospora, Paecilomyces, Penicillium, Phycomyces, Phyllostricta, Pythium, Rhizopus, Septoria, Sphaceloma, Trichoderma, Trichosporon, Trichurus and Verticillium;

inoculating a liquid growth medium comprising phenylacetic acid with a fungal biomass taken from the solid growth medium culture;

cultivating the fungus in the liquid growth medium until the phenylacetic acid is metabolized to 2-hydroxyphenylacetic acid; and recovering the 2-hydroxyphenylacetic acid from the liquid growth medium.

2. A process as claimed in claim 1, wherein a fungus of the genus Humicola or Chaetomium is used as microorganism.

3. A process as claimed in claim 1, wherein the fungus DSM 7047 is used as microorganism.

4. A biologically pure fungus of the genus Humicola or Chaetomium which is deposited under deposit number DSM 7047.

* * * * *